(12) United States Patent
Ando et al.

(10) Patent No.: US 6,706,129 B2
(45) Date of Patent: Mar. 16, 2004

(54) METHOD FOR MANUFACTURING PARTICLE DEPOSITED BODY

(75) Inventors: Kenji Ando, Tochigi-ken (JP); Kenichi Sato, Tochigi-ken (JP); Yasuhiro Umeki, Tochigi-ken (JP); Hiroshi Hirasawa, Tochigi-ken (JP); Kazuyuki Maeda, Tochigi-ken (JP)

(73) Assignee: Kao Corporation, Tokyo (JP)

( * ) Notice: Subject to any disclaimer, the term of this patent is extended or adjusted under 35 U.S.C. 154(b) by 138 days.

(21) Appl. No.: 09/726,493

(22) Filed: Dec. 1, 2000

(65) Prior Publication Data

US 2001/0006089 A1 Jul. 5, 2001

(30) Foreign Application Priority Data

Dec. 22, 1999 (JP) ............................................ 11-363650

(51) Int. Cl.⁷ ................................................. A61F 13/00
(52) U.S. Cl. ...................... 156/62.2; 156/276; 156/209; 156/324; 264/518; 264/121; 264/122
(58) Field of Search ................................. 264/517, 518, 264/122, 121, 119, 112; 156/62.2, 62.8, 285, 296, 276, 324, 209; 19/145, 301

(56) References Cited

U.S. PATENT DOCUMENTS

| 3,860,002 | A | | 1/1975 | Kolbach |
|---|---|---|---|---|
| 4,551,191 | A | | 11/1985 | Kock et al. |
| 4,761,258 | A | | 8/1988 | Enloe |
| 4,787,947 | A | * | 11/1988 | Mays .......................... 156/160 |
| 5,393,599 | A | * | 2/1995 | Quantrille et al. ............. 442/57 |
| 5,494,622 | A | | 2/1996 | Heath et al. |
| 5,759,678 | A | * | 6/1998 | Fujii et al. .............. 210/500.27 |
| 5,766,388 | A | * | 6/1998 | Pelley et al. ................. 156/204 |
| 5,916,670 | A | * | 6/1999 | Tan et al. .................... 428/219 |

FOREIGN PATENT DOCUMENTS

EP 0627211 12/1994

* cited by examiner

Primary Examiner—Jeff H. Aftergut
Assistant Examiner—Barbara J Musser
(74) Attorney, Agent, or Firm—Birch, Stewart, Kolasch & Birch, LLP

(57) ABSTRACT

There is disclosed a method for manufacturing particle deposited body comprising supplying, under sucking condition, particles entrained by air on a continuous carrier sheet which is running at a prescribed direction to deposit the particles on the carrier sheet, thereby obtaining a particle deposited body comprising the particles and the carrier sheet, the carrier sheet having an air-permeability of 4.0 seconds/(300 ml·32 pcs.) or less.

4 Claims, 3 Drawing Sheets

METHOD FOR MANUFACTURING PARTICLE DEPOSITED BODY

BACKGROUND OF THE INVENTION

This invention relates to a method for manufacturing a particle deposited body and more particularly to a method for manufacturing a particle deposited body, which is capable of effectively manufacturing a particle deposited body suited to be used for manufacturing an absorbent core in an absorbent article such as a disposable diaper, a sanitary napkin and the like.

A method and an apparatus for scattering particles on a porous web are disclosed in U.S. Pat. No. 4,551,191. In the method and the apparatus disclosed in U.S. Pat. No. 4,551,191, however, although it is possible to scatter particles so as to be uniformly dispersed on a porous web, it is impossible to deposit the particles thereon in a desired pattern. Moreover, it is difficult to make the transfer speed of the porous web at a high speed and it is also impossible to make a continuous production of a deposited body of particles used for, among others, manufacturing an absorbent core at a high speed.

SUMMARY OF THE INVENTION

It is, therefore, an object of the present invention is to provide a method for manufacturing a particle deposited body, which is capable of making a continuous production of a particle deposited body suited to be used for manufacturing an absorbent core in a disposable diaper, a sanitary napkin, etc., at a high speed and which is capable of making the contour of the deposited portion of the particles in a desired pattern at that time.

The present invention has achieved the above object by providing a method for manufacturing particle deposited body comprising supplying, under sucking condition, particles entrained by air on a continuous carrier sheet which is running at a prescribed direction to deposit the particles on the carrier sheet, thereby obtaining a particle deposited body comprising the particles and the carrier sheet, the carrier sheet having an air-permeability of 4.0 seconds/(300 ml·32 pcs.) or less. It should be noted that the expression "particles are deposited on a carrier sheet" used herein includes not only a concept in which the particles are deposited on or in the carrier sheet but also a concept in which the particles are deposited on or in another sheet(s) which is laminated on the carrier sheet.

BRIEF DESCRIPTION OF THE DRAWINGS

The present invention will be more particularly described with reference to the accompanying drawings, in which.

DETAILED DESCRIPTION OF THE PREFERRED EMBODIMENTS

One preferred embodiment of the present invention will be described hereinafter. First, an apparatus for manufacturing a particle deposited body, which is suited for a method for manufacturing a particle deposited body according to this embodiment, will be described.

Figure 1:
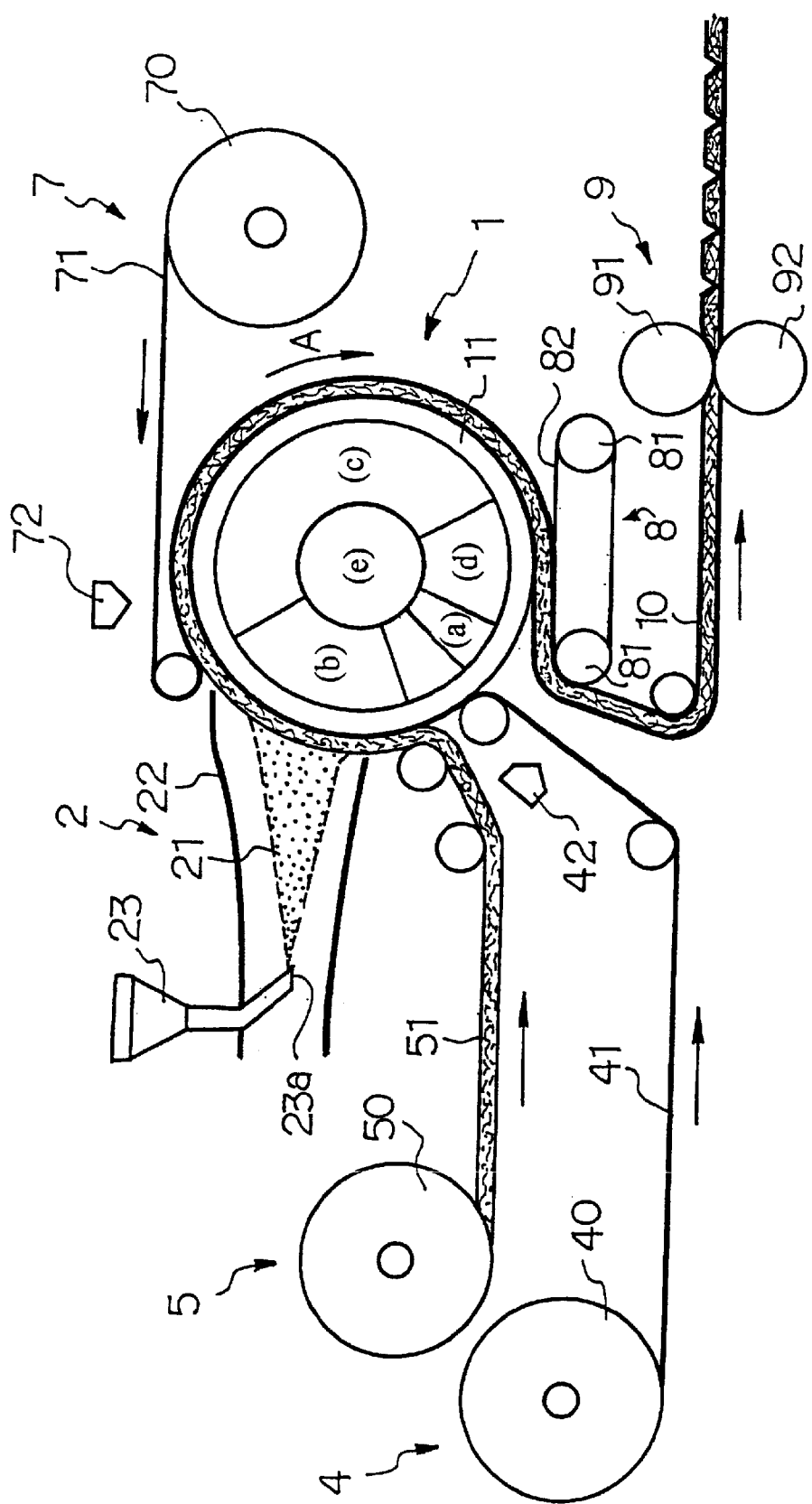
FIG. 1 is a schematic view showing an apparatus for manufacturing a particle deposited body which is favorably used for carrying out a method for manufacturing a particle deposited body according to the present invention.

An apparatus for manufacturing a particle deposited body shown in FIG. 1 is an apparatus for manufacturing an absorbent core continuous body to be cut to a prescribed length and eventually formed into an absorbent core of a sanitary napkin such as a paper diaper, a sanitary napkin, etc. It comprises a depositing apparatus 1 including a rotary drum 11 on an outer peripheral surface of which a plurality of particle sucking portions are formed at predetermined intervals and adapted to suck air which entrains particles from the particle sucking portions and deposit the particles thereon, and a particle supplying mechanism 2 for supplying the particles toward the depositing apparatus 1 by entraining by air stream.

This manufacturing apparatus further comprises a carrier sheet supplying mechanism 4 for supplying an air-permeable carrier sheet in such a manner as to wind the carrier sheet around the outer peripheral surface of the rotary drum 11, a retaining sheet supplying mechanism 5 for supplying a retaining sheet 51 onto the carrier sheet 41 before particles 21 are deposited thereon, a cover sheet supplying mechanism 7 for supplying a cover sheet 71 onto the carrier sheet 41, more strictly, onto the retaining sheet 51 on the carrier sheet 41 after the particles 21 are deposited on the carrier sheet 41, a deposited body leading-out and transferring mechanism 8 for leading out the carrier sheet 41, the retaining sheet 51 and the cover sheet 71 (particle deposited body 10) with the particles 21 retained in or between the sheets from the top of the rotary drum 11 and transferring them, and an embossing apparatus 9 for applying an embossing treatment to the particle deposited body 10 which has been lead out and transferred.

The rotary drum 11 in the depositing apparatus 1 exhibits a cylindrical configuration and is rotation driven in one direction as indicated by an arrow A of FIG. 1. A plurality of particle sucking portions (not shown) each having a predetermined configuration are formed on the outer peripheral surface at predetermined intervals in its circumferential direction. The particle sucking portions are portions including a number of pores which are capable of sucking air. Each particle sucking portion is formed with a number of pores over an entire surface thereof. More specifically, the outer peripheral surface of the rotary drum 11 is composed of a net-like member and the net-like member is provided with an air-permeable portion and an air-impermeable portion. The air-permeable portion is formed with the pores, while the air-impermeable portion is not formed with the pores. The air-permeable portion is arranged so as to exhibit a predetermined configuration, thereby forming the particle sucking portions. The particle sucking portions may take any desired configuration, such as elliptical, rectangular, diamond, circular, center-narrowed rectangular, or the like. The configuration of the particle sucking portions is not particularly limited.

The rotary drum 11 is connected with a suction fan (not shown) through a suction duct (not shown). The suction fan is driven so that the pressure at a prescribed portion inside the rotary drum 11 be kept negative. During the time the particle suction portions pass the location where the internal pressure is negative, the pores formed in the particle suction portions function as suction holes. Moreover, the intake of air from the particle suction portions generates an air-stream capable of delivering the particles 21 towards the rotary drum 11, within a duct 22 one end of which covers the outer peripheral surface of the rotary drum 11.

The particle supplying mechanism 2 comprises the duct 22, an introduction apparatus 23 for introducing the particles into the duct 22 and the suction fan for generating an air-stream within the duct 22. The introduction apparatus 23 is designed such that the particles 21 are supplied into the air-stream generated within the duct 22 in the dispersed states (either only single kind of or plural kinds of the particles). The introduction apparatus 23 includes a supply position adjusting mechanism for changing the location of a particle inlet port 23a. The particle inlet port 23a can be moved, by a known mechanism, in a back and forth direction along the air-stream and in a vertical direction orthogonal to the air-stream.

The rotary drum 11, as shown in FIG. 1, has four chambers (a), (b), (c) and (d) defined therein. Those chambers (a), (b), (c) and (d) are adapted to exert different suction forces to the particle suction portions. The rotary drum 11 also has a center chamber (e) likewise defined therein. A suction duct (not shown) is connected to the center chamber (e). A damper is attached to a partition between the center chamber (e) and the four chambers (a)–(d) or between the two chambers (b) and (c) and a rotary drum ring so that the sucking air amount/static pressure can be adjusted in each chamber separately. The chambers (b) and (c) are maintained to negative pressure.

The sucking air amount/static pressure is set largest in the chamber (b) which is intended to suck air. From the viewpoint for ensuring the arrangement and fixture of the particles to the inside of the retaining sheet, the static pressure is preferably −5 kPa or more and particularly preferably −8 kPa or more, and the maximum air velocity within the duct 22 is preferably 5 m/s or more and particularly preferably 15 m/s or more. As the means for increasing the air velocity, the sectional area of the duct may be reduced or the capacity of the suction fan may be increased. In order to suck and retain the sheet and the particles on the drum surface, a required air amount/static pressure is applied to the chambers (b) and (c). The chambers (a) and (d) are cut off the connection with the suction fan. The chamber (d) is connected with an air blower and its inside is maintained to positive pressure, thereby enabling the easy peel-off of the web from the drum so that a smooth supply to the next process can be executed. The chamber (a) preferably has the function for clean the net-like or mesh-like particle suction portions on the surface of the rotary drum 11.

The carrier sheet supplying mechanism 4, the retaining sheet supplying mechanism 5 and the cover sheet supplying mechanism 7 each comprise a driving roller, a guide roller or the like. Those mechanisms 4, 5 and 7 continuously pay out the respective sheets, respectively from web rolls 40, 50, 70 and supply them from predetermined positions in the peripheral direction of the rotary drum 11 on to the outer peripheral surface of the rotary drum 11 in this order.

The deposited body leading-out and transferring mechanism 8 comprises a known continuously transferring mechanism including a pair of rollers 81, 81 and an endless belt 82 disposed therebetween, and a transfer mechanism (not shown) such as a vacuum apparatus located at a lower part of the rotary drum 11 and adapted to lead out the particle deposited body 10 onto the endless belt 82.

The embossing apparatus 9 is an apparatus for applying a thermal embossing to the particle deposited body 10 which has been led out. In the embossing apparatus 9, the particle deposited body 10 is inserted between a pair of embossing rolls 91, 92 so that the compositions, which compose the particle deposited body 10, are integrated by heat fusing.

An apparatus for manufacturing a particle deposited body using the above particle deposited body manufacturing apparatus will now be described. First, the depositing apparatus 1, the carrier sheet supplying mechanism 4, the retaining sheet supplying mechanism 5, the cover sheet supplying mechanism 7, the deposited body leading-out and transferring apparatus 8 and the embossing apparatus 9 are actuated, and the suction fan of the particle supplying mechanism 2 is also actuated to generate an air stream within the duct 22. Then, a high absorption polymer or the like, is introduced, as the particles 21, into the duct 22 from the introduction apparatus 23 of the particle supplying mechanism 2.

Owing to the above arrangement, the carrier sheet 41, the retaining sheet and the cover sheet 71 are supplied to the rotary drum 11 in this order. Moreover, the particles 21 which are entrained by air are supplied onto the carrier sheet 41 between the supply position of the retaining sheet 51 and the supply position of the cover sheet 71. The supplied particles 21 are deposited in the retaining sheet 51 on the carrier sheet 41 and the deposited particles 21 are stably retained in the retaining sheet 51 by being covered with the cover sheet 71. By doing so, a belt-like laminated body (particle deposited body 10) composed of the carrier sheet 41, the retaining sheet 51 and the cover sheet 7 with the particles 21 retained therein is continuously manufactured. The particle deposited body 10 is subjected to embossing treatment by the embossing apparatus 9 and integrated.

The carrier sheet 41 must have a favorable air-permeability so that transferring of the particles by a suction air and deposition of the particles onto the suction surface are not interrupted. From the viewpoint for preventing the accidental passage of the particles, the oozing-out at the time of using a hot melt type adhesive agent and the occurrence of inconveniences against the stable processing caused by decrease in strength of the carrier sheet, the air-permeability of the carrier sheet is 4.0 seconds/(300 ml·32 pcs.) or less and preferably 3.0 seconds/(300 ml·32 pcs.) or less. Moreover, from the same viewpoint, the average pore diameter of the carrier sheet is preferably an average diameter or less of the particles to be used. As one specific example of the average pore diameter of the carrier sheet is preferably 200 μm or less and more preferably 100 μm or less. Moreover, from the same viewpoint as above, the strength of the carrier sheet in a dried state is preferably 60 cN/25 mm or more in the CD direction and 150 cN/25 mm or more in the MD direction, more preferably 500 cN/25 mm or more in the MD direction and particularly preferably, 800 cN/25 mm or more in the MD direction.

The air-permeability can be measured in accordance with JIS-P8117 as follows. The carrier sheet 41 is cut into 70×70 mm and then 32 cut pieces of the carrier sheet 41 thus obtained are stacked up. Then, the time required for the air of 300 ml to permeate through the stack-up cut pieces is measured using an air permeation measuring device [GURLEY DENSOMETER (Merchandise Name) manufactured by Kumagaya Riki Kogyo K. K.].

The strength of the carrier sheet 41 in its dried state in the MD and CD directions can be measured, respectively, as follows. As for the strength in the MD direction, a test piece is cut out having a length of 150 mm in the same direction (MD) as the flowing direction at the time of manufacture and a width of 25 mm in the direction (CD) perpendicular to the flowing direction and this test piece is subjected to tensile test under the conditions of a chuck-to-chuck distance of 50 mm and a pull speed of 300 mm/min in the MD direction, using a Tensilon tensile tester (manufactured by Orientic K. K.). Then, the breaking strength at that time is measured.

Similarly, as for the strength in the CD direction, a test piece is cut out having a length of 25 in the MD direction and a length of 150 mm in the CD direction and this test piece is subjected to tensile test under the conditions of a chuck-to-chuck distance of 50 mm and a pull speed of 300 mm/min in the CD direction, using the above Tensilon tensile tester. Then, the breaking strength is measured in the same manner.

As the carrier sheet 41, a sheet of paper or a nonwoven fabric is preferred.

Particularly, a sheet of paper having a basis weight of 5 to 50 g/m2 is preferred. In the case where the carrier sheet 41 has the function of the retaining sheet 51 and the retaining sheet 51 is omitted, a nonwoven fabric is preferred, and the nonwoven fabric, which is preferred particularly as the retaining sheet 5, is as later described. Furthermore, as the carrier sheet 41, a woven fabric and a perforated film may be used.

The retaining sheet 51 is a sheet which is used in the case where the carrier sheet 41 does not have the function for retaining the particles 21 or the retaining function had by the carrier sheet 41 is insufficient. It is essentially required for the retaining sheet 51 to have a favorable air-permeability and not to disturb the transferring of the particles by the suction air and depositing of the particles onto the suction surface. Particularly, the retaining sheet 51 preferably has the capability for maintaining the particles, which have been dispersed in the thickness direction, in predetermined states.

As the retaining sheet 51, a nonwoven fabric, a sheet of paper, a cloth or the like, which are capable of retaining the particles among fibers, may be used. Among them, the nonwoven fabric is preferably used. In the case where the nonwoven fabric is used, the particles 21 enter voids in the retaining sheet 51 and a thin particle deposited body bested suited for manufacturing a thin absorbent core can be obtained.

A sheet as the retaining sheet 51 is a sheet which is capable of retaining the particles among the fibers, which does not prevent the particles from getting swollen when they absorb liquid and whose inter-fiber structure of its composing fiber is such that a distance between fiber-to-fiber is changed (enlarged) as the particles are swollen. As a sheet having such a construction, there can be listed a nonwoven fabric which has an adhered crossing point as a crossing point between the composing fibers and a non-adhered crossing point which is either not adhered at all or merely so weakly adhered that the adhesion is released during the swelling process of the particles. Specifically, the examples of a preferred sheet as the retaining sheet 51 may include a nonwoven fabric composed of a thermofusible fiber and a non-thermofusible fiber, a nonwoven fabric which is composed of a first thermofusible fiber and a second thermofusible fiber different therefrom and in which the heat adhering force between the first thermofusible fiber and the second thermofusible fiber is smaller than the heat adhering force between the first thermofusible fibers themselves or between the second thermofusible fibers themselves or the first thermofusible fibers are not heat adhered to the second thermofusible fibers.

The embodiment in which the retaining sheet 51 is supplied onto the carrier sheet 41, is particularly useful in the case where the retaining sheet 51 is bulky, readily extensible, lack in strength or porous. In the case where the carrier sheet 41 can exhibit its sufficient function for retaining the particles 21, the retaining sheet 51 may be omitted.

It is preferred that when the retaining sheet 51 is supplied onto the carrier sheet 41, the carrier sheet 41 and the retaining sheet 51 are adhered together by an adhesive agent so that the sheets 41, 51 are integrated. In this embodiment, as shown in FIG. 1, before the retaining sheet 51 is laminated on the carrier sheet 41, a hot-melt type adhesive agent is applied to the carrier sheet 41 by an adhesive agent applying apparatus 42 and the sheets 41, 51 are integrated through the hot-melt adhesive agent. By adhering the carrier sheet 41 and the retaining sheet 51 together through an adhesive agent, preferably through a hot-melt type adhesive agent, such shortcomings of a sheet as readily expansible or low in strength can be offset by the other sheet. For a porous sheet, such shortcomings as accidental passage of polymer and contamination of the particle suction portions of the rotary drum caused thereby can be prevented.

As an apparatus for applying a hot-melt type adhesive agent, there can be used a non-contact type sprayer, a non-contact type bead gun, a non-contact type slot coater, a gravure coater, screen coater or the like may also be used. In general, since the contact type coater tends to catch a waste or foreign matter at its contact point thereby adversely affecting the coating condition, the use of a non-contact type coater is preferred. Moreover, it is preferred that the adhesive agent is applied in a mesh-like fashion, because the adhesive strength can be obtained with a comparatively small amount of adhesive agent without degrading the liquid absorption. As the coating apparatus, a non-contact type sprayer designed for splaying for a bead or fiber, such as a spiral sprayer, a curtain sprayer or the like is preferred.

The particles 21 supplied from the introduction apparatus 23 are entrained by air and deposited on the retaining sheet 51 laminated on the carrier sheet 41. The particles 21 enter the voids in the retaining sheet 51 and deposited in the thickness direction in the desired dispersed states. The particles 21 are deposited such that the contour of the deposited portion of the particles 21 exhibits substantially same in configuration as the particle suction portions in a plan view of the sheet.

As the particles 21 for manufacturing a continuous body of an absorbent core as a particle deposited body, there can be used various kinds of known high absorption polymer and deodorant, fragrant, etc. may be used. For example, as the high absorption polymer, poly (sodium acrylate), copolymer of acrylic acid and vinylalcohol, crosslinked poly (sodium acrylate), graft copolymer of starch and acrylic acid, copolymer of isobutylene and maleic anhydride and saponified material thereof, polyaspartic acid, or the like may be used without any particular limitation.

The kind of the particles 21 supplied from the particle supplying mechanism 2 may be single or plural. In the case where plural kinds of particles 21 are supplied, the deposited state of the particles can be made into a desired scattered state by controlling the arriving positions of the plural kinds of particles on the outer peripheral surface of the rotary drum 11. The expression "plural kinds" used here refers to two or more kinds of particles which are different in any of composition, grain diameter, density, shape (spherical, mass), etc.

For example, as shown in FIG. 2, as the particles 21, different kinds of particles a, b are introduced out of the introduction apparatuses 23, 23, respectively. At that time, plural kinds of particles having different physical properties are used or the introducing conditions at the time for introducing the particles into the air stream are changed for each different kind of particles. By doing so, the arriving positions of the plural kinds of particles on the outer peripheral surface of the rotary drum can be controlled and the deposited states in the thickness direction of the plural kinds of particles can be made into the desired scattered states.

Figure 2A:
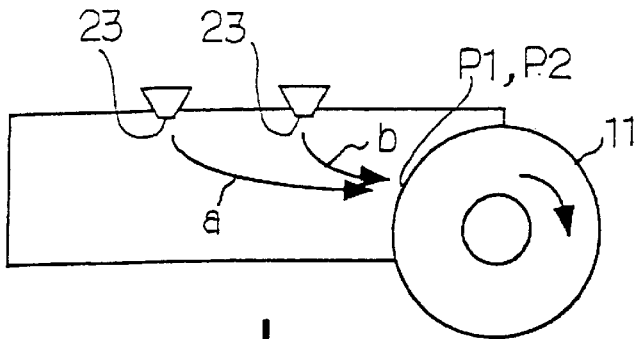
FIG. 2(a), FIG. 2(b), FIG. 2(c) and FIG. 2(d) are each schematic views for explaining one example of a method for controlling arrival positions of plural kinds of particles in one embodiment of the present invention.
Figure 2B:
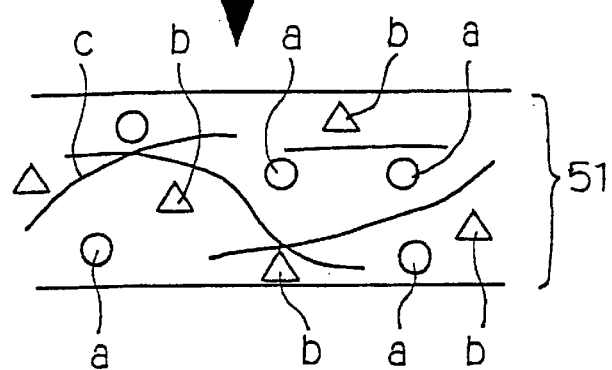
Figure 2C:
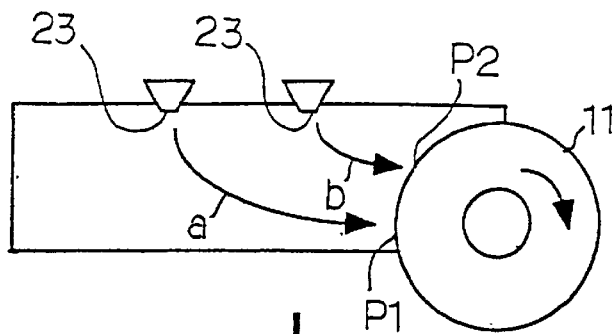
Figure 2D:
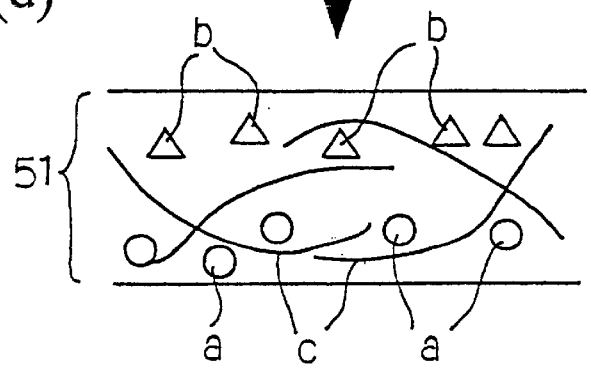

That is, as shown in FIG. 2(a), by coinciding the arriving positions P1, P2 of two kinds of particles a, b on the outer peripheral surface of the rotary drum 11, the particles a, b can be deposited in the evenly mixed states in the thickness direction of the retaining sheet 51 as shown in FIG. 2(b). Moreover, as shown in FIG. 2(c), by changing the arriving positions P1, P2 of the two kinds of particles a, b on the outer peripheral surface of the rotary drum 11, the particles a, b can be deposited such that they form different layers in the thickness direction of the retaining sheet 51 as shown in FIG. 2(d). Reference symbol c of FIGS. 2(b) and 2(d) denotes a fiber composing a nonwoven fabric in the case when the nonwoven fabric is used as the retaining sheet 51.

The expression "physical properties" used in the above description reading partly "plural kinds of particles having different physical properties" refers to grain diameter, density of the particles, etc. Similarly, the expression "introducing conditions" used in the above description partly reading as "the introducing conditions . . . are changed for each different kind of particles" as means for controlling the arriving positions of the particles, refers to "introducing positions", "initial introducing speed", "introducing angle", etc. From the viewpoint of easy controlling, at least one of the introducing positions, the initial introducing speed and the introducing angle is changed for each supplying apparatus, i.e., for each different kind of particles is preferably made different. As means for making different of the initial introducing speed, there may be used means for installing an air blower at the particle inlet portion. An apparatus, which is different in the particle inlet port but in which the remaining parts are commonly used, is also included in the concept of the "different apparatus". Moreover, as the method for controlling the arriving positions of the plural kinds of particles, those particles having different physical properties from each supplying apparatus may be introduced in different introducing conditions.

After the particles 21 are deposited on the carrier sheet 41, the top surface on which the particles 21 are deposited is covered with the cover sheet 71. By sandwiching the retaining sheet 51 retaining the particles 21 between the carrier sheet 41 and the cover sheet 71, accidental dropping of the particles in the process to follow can be prevented. A hot-melt type adhesive agent is applied to the cover sheet 71 by an adhesive agent applying apparatus 72, so that the cover sheet 71 integrally adhered to the retaining sheet 51 on which the particles are deposited. As the adhesive agent applying apparatus 72, a similar apparatus to an adhesive agent applying apparatus 42 for applying an adhesive agent between the carrier sheet 41 and the retaining sheet 51 may be used. The cover sheet 71 is employed not only for the purpose to prevent the processing particles from dissipating but also to prevent the particles from accidentally dropping during the time for heat embossing which is performed in the process to follow. The cover sheet 71 is also adapted to prevent leakage and dropping of the particles in the case the particle deposited body is incorporated in an absorbent article and worn by a wearer.

The covering with the cover sheet 71 is a preferred example of means for preventing the dissipation of the particles. Other preferred examples of the means for preventing the dissipation of the particles, there are a C fold, a double fold of the carrier sheet itself, etc. This means for preventing the dissipation of the particles is preferably applied immediately after the end of the depositing process of the particles. However, it is also accepted that the means for preventing the dissipation of the particles is not applied immediately after the end of the depositing process because the deposited particles can be transferred while pressing the deposited particles with a transportation belt or suckingly retaining the deposited particles by vacuum, or the like.

The belt-like particle deposited body 10 comprising the carrier sheet 41, the retaining sheet 51 and the cover sheet 71 is transferred to a lower part of the rotary drum 11 while maintaining the dispersed states of the particles, and then led out from the rotary drum 1 by the deposited body leading-out and transferring mechanism 8.

The particle deposited body 10 led out from the rotary drum 11 is applied with an embossing treatment by the embossing apparatus 9 and integrated. The embossing treatment is preferably a heat embossing. The heat embossing is preferably applied such that a number of small chambers each having a small area are formed in the particle deposited body 10 so that even in the case the particle deposited body 10 is incorporated in an absorbent article and worn by a wearer, the particles 21 are not undesirably moved only to one side and located there. For example, a lattice-like embossing treatment is preferably applied to the particle deposited body 10 by a press member having pressing ridge formed in a lattice-like pattern thereon. It is also effective for preventing the one-sided location of the particles of high absorption polymer or the like that a hot-melt type adhesive agent is disposed at the pressing part to be pressed during the embossing treatment, the cover sheet 71 and the carrier sheet 41 are adhered at the pressing part, thereby partitioning the small chambers by the adhesion achieved by the hot-melt type adhesive agent so that a number of closed parts are provided. In order to make the heat embossing effective, the sheets composing the particle deposited body 10 preferably includes a thermofusible fiber.

Figure 3:
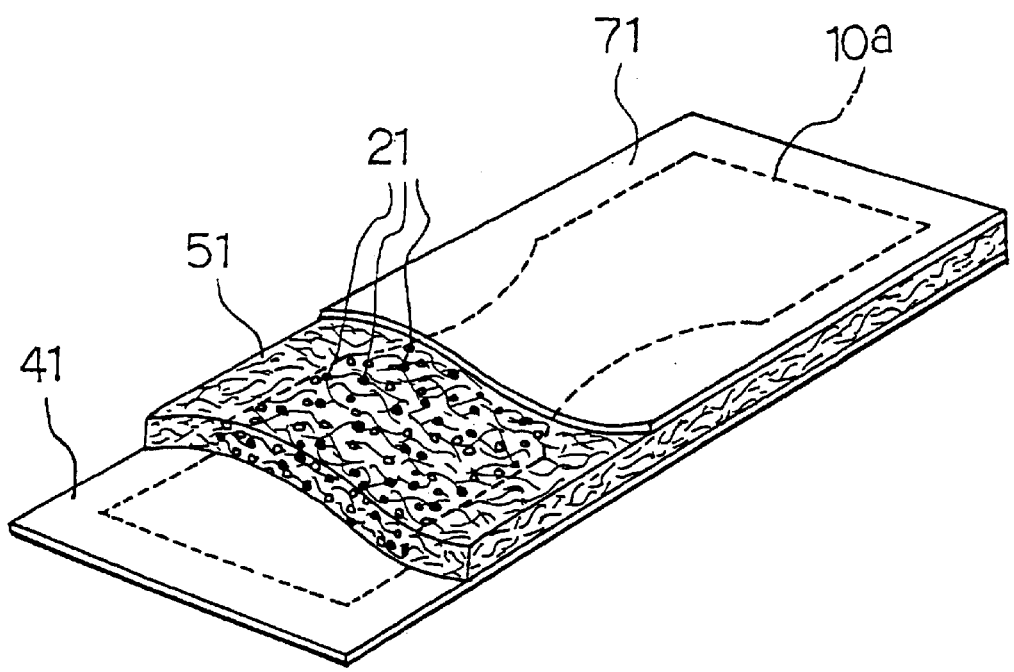
FIG. 3 is a partly broken perspective view showing a laminated structure of a particle deposited portion of the particle deposited body.

Each particle deposited body 10 obtained in this embodiment is a belt-like continuous body of an absorbent core which is composed by arranging a number of particle deposited parts (that part where the particles 21 are deposited) having a predetermined configuration at predetermined intervals in the longitudinal direction on an elongated belt-like configuration comprising the carrier sheet 41, the retaining sheet 51 and the cover sheet 71 each having an elongated belt-like configuration. In the retaining sheet 13 at the particle deposited parts, the particles 21 (high absorption polymer) are retained in a desired dispersed states in the thickness direction. FIG. 3 shows a lamination structure of the particle deposited body 10 at its particle deposited part 10a. After applied with the embossing treatment by the embossing apparatus 9, the particle deposited body 10 is cutting into individual lengths, which absorbent articles such as sanitary napkins have, by cutting between the particle deposited parts and used as absorbent cores for the individual absorbent articles. Particularly, in the form of FIG. 3, accidental dropping of the particles from the end part can be prevented.

As mentioned above, according to a method for manufacturing a particle deposited body of this embodiment, a particle deposited body (absorbent core continuous body) suited for manufacturing an absorbent core in a disposable diaper, a sanitary napkin, etc. can be continuously produced at a high speed.

Moreover, according to a method for manufacturing a particle deposited body of this embodiment, the particles are entangled with the fibers composing the carrier sheet 41 and/or retaining sheet 51. By doing so, a particle deposited body, in which particles are prevented from being overly one-sided, can be manufactured at a high speed and in a stable manner, without allowing the accidental dropping of the particles during processing. Since the particle suction portions having a predetermined configuration is formed on the outer peripheral surface of the rotary drum 11 and the particles are deposited such that the contour of the deposited part of the particles exhibits substantially the same configuration as the particle suction portions, a particle deposited body including a particle deposited part having a desired configuration corresponding to that of the particle suction portions can be formed easily and with an enhanced productivity.

Moreover, by continuously forming the particle suction portions on the rotary drum 11 over the entire surface in the peripheral direction, there can also be manufactured a particle deposited body including the particle deposited portions continuously formed over the longitudinal direction. In this way, according to a method for manufacturing a deposited body of the present invention, by forming the particle suction portions into a desired configuration, the particles can be intermittently or continuously scattered. In either case, the particle deposited body, which is a portion where the particles are deposited, can be formed in a desired configuration. The contour of the particle deposited portions (portion where the particles are deposited) is extremely sharp.

Moreover, according to the manufacturing method of this embodiment, by using plural kinds of particles having different physical properties as the particles or setting the introducing conditions differently for each different kind of particles at the time of introducing the air stream, the arriving positions of the plural kinds of particles on the outer peripheral surface of the rotary drum are properly controlled. By doing so, there can easily be manufactured a particle deposited body in which plural kinds of particles are deposited in the retaining sheet in the desired dispersed states. From the viewpoint of obtaining a particle deposited body in which the particles are hardly suffered from gel blocking during swelling of the particles and the absorptive performance thereof is enhanced, the particles 21 are preferably evenly dispersed in the retaining sheet 51 over the thickness direction.

In the case where the particle deposited body obtained by this manufacturing method is used as an absorbent core of an absorbent article, the absorbent core can be made thin without sacrificing the excellent absorbing performance of the high absorption polymer. Thus, even in the case where the absorbent core is made light in weight and compact in size, it can exhibit an excellent absorbing performance. Since the high absorption polymer is firmly secured to the retaining sheet, it can fully withstand the twisting and breakage of the absorbent core and leakage caused by the twisting, etc. can be restrained.

As another embodiment of the present invention, it is also accepted that a belt-like carrier sheet having an air-permeability of 2.0 seconds/(300 ml·32 pcs.) or less is continuously supplied onto a mesh conveyor as a depositing apparatus, then particles are supplied in their dispersed states onto the carrier sheet, and then the particles are sucked through particle suction portions formed in the mesh conveyor so as to be deposited on the carrier sheet, there by manufacturing a particle deposited body including the carrier sheet and the particles. It is also accepted that after the particles are deposited on the carrier sheet 41, the above-mentioned various dissipation preventing means may be applied thereto. In this embodiment, since the particles can be dropped and deposited by their own dead weight, the particles can be deposited with a less air velocity compared with the case wherein a drum type depositing apparatus is used. Moreover, other depositing apparatus equipped with the particle suction portions may be used.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for manufacturing a particle deposited body, comprising:
   supplying a continuous carrier sheet which is running in a prescribed direction and having a tensile strength in the MD direction of 500 cN/25 mm or more;
   supplying a retaining sheet onto said carrier sheet;
   providing a partial vacuum behind said carrier sheet and retaining sheet so as to draw air therethrough in a thickness direction of the retaining sheet, said carrier sheet having an air-permeability of 4.0 seconds/(300 ml·32 pcs.) or less;
   entraining particles by air so as to deposit said particles into said retaining sheet to obtain a particle deposited body in which the particles are retained throughout the thickness direction of said retaining sheet.

2. The method for manufacturing a particle deposited body according to claim 1 wherein said air is sucked by a particle sucking portion which is formed in a predetermined configuration and the particles are deposited such that a contour of a deposited portion of the particles has a generally same configuration as said particle sucking portion.

3. The method for manufacturing a particle deposited body according to claim 1 wherein after the particles are deposited on said carrier sheet, dissipation preventing means for preventing dissipation and dropping of the particles is applied.

4. The method for manufacturing a particle deposited body according to claim 3, wherein after said dissipation preventing means is applied, said particle deposited body is subjected to embossing treatment and materials composing said particle deposited body are integrated.

* * * * *